(12) United States Patent
Mangino

(10) Patent No.: US 8,067,150 B2
(45) Date of Patent: Nov. 29, 2011

(54) IN-SITU PRESERVATION (ISP) BRIDGE METHOD AND SOLUTION FOR NON-HEART BEATING DONORS

(75) Inventor: Martin J. Mangino, Powhatan, VA (US)

(73) Assignee: Virginia Commonwealth University, Richmond, VA (US)

( * ) Notice: Subject to any disclaimer, the term of this patent is extended or adjusted under 35 U.S.C. 154(b) by 415 days.

(21) Appl. No.: 12/159,923

(22) PCT Filed: Jan. 9, 2007

(86) PCT No.: PCT/US2007/060269
§ 371 (c)(1),
(2), (4) Date: Jan. 14, 2009

(87) PCT Pub. No.: WO2007/082203
PCT Pub. Date: Jul. 19, 2007

(65) Prior Publication Data
US 2009/0298043 A1    Dec. 3, 2009

(51) Int. Cl.
*A01N 1/00* (2006.01)
*A01N 1/02* (2006.01)

(52) U.S. Cl. .................................. 435/1.1; 435/1.2

(58) Field of Classification Search .................. None
See application file for complete search history.

(56) References Cited

U.S. PATENT DOCUMENTS 7,005,253 B2    2/2006  Polyak
2004/0053205 A1  3/2004  Potts et al.

FOREIGN PATENT DOCUMENTS

WO        WO 02/30452 A1    4/2002

OTHER PUBLICATIONS

Dubey et al., "Anti-inflammatory action of diltiazem in patients with unstable angina", Postgrad. Med. J. 82 : 594-597 (2006).*

* cited by examiner

*Primary Examiner* — Sandra Saucier
(74) *Attorney, Agent, or Firm* — Whitham Curtis Christofferson & Cook, PC

(57) ABSTRACT

A method for rapid, in-situ flushing of organs of a non-heart beating donor, and solutions for carrying out the flushing, are provided. The method initiates organ preservation, and the solutions are formulated to counteract basic mechanisms of ischemic cell injury, and to activate known biochemical survival pathways in the cell. Viability of the organ for transplant is thus maintained.

4 Claims, 2 Drawing Sheets

IN-SITU PRESERVATION (ISP) BRIDGE METHOD AND SOLUTION FOR NON-HEART BEATING DONORS

BACKGROUND OF THE INVENTION

1. Field of the Invention

The invention generally relates to the preservation of organs for organ transplant. In particular, the invention provides a method of rapid, in-situ flushing of organs to initiate cooling and preservation in non-heart beating donors, as well as solutions formulated to counteract basic mechanisms of cell injury during ischemia and activate known biochemical survival pathways in the cell.

2. Background of the Invention

The donation of internal organs is an important and often crucial aspect of health care. The technology for carrying out organ transplants and for maintaining the health of transplant recipients has advanced greatly in the last decade. Unfortunately, the largest hurdle for transplant procedures is not know-how, but rather the lack of availability of healthy organs to transplant.

Most organs are harvested from transplantation from cadaveric patients with brain death. During a brain death organ harvest, the heart continues to beat and supplies the organs with blood and oxygen until they are cooled and removed. However, most patients that are potential organ donors do not die from brain death but rather cardiac death, which is characterized by cessation of heart beat with rapid loss of oxygen to warm organs (ischemia) Non-heart beating donors (NHBDs) (i.e. these patients exhibiting irreversible cardiac death) are a potential source of healthy organs for donation. Conventional organ harvest from NHBDs involves either simply removing the organs after cardiac death, or removal of organs after the donor has been placed on cardiopulmonary bypass after cardiac death. Unfortunately, the former procedure does nothing to rapidly initiate organ preservation, and the latter procedure is often initiated belatedly due to the cumbersome and complex nature of cardiopulmonary bypass. For example, human kidneys are able to tolerate up to about 60 minutes of warm ischemia, but conventional organ harvesting techniques typically result in a warm ischemia period of at least 90 to 180 minutes, which is lethal to kidneys. Kidneys obtained from NHBDs by conventional organ harvest usually cannot, therefore, be used for transplant. This represents a terrible waste of otherwise potentially viable organs, which, for a wait-listed transplant candidate, could make the difference between leading a relatively normal life and suffering tragic, debilitating illness or death.

The prior art has thus-far failed to provide a method to rapidly initiate and support organ preservation in NHBDs, or to provide protection from the impending periods of warm ischemia and reperfusion injury in this group of donors. This is necessary in order to maintain the organs' suitability for use in transplantation.

SUMMARY OF THE INVENTION

The present invention provides methods of rapidly initiating the preservation of internal organs in-situ in non-heart beating donors. The method bridges the gap between the time of an organ's earliest initial ethical availability, and the time when the organ can actually be removed from the donor's body and subjected to conventional harvesting and preservation procedures. The method involves focused, rapid cooling of an organ in-situ by permeating the organ with a cold flushing solution that is specially formulated to counteract the deleterious effects of ischemia and prolonged hypothermia. According to the invention, the flushing solution is delivered to an isolated segment of a biological conduit (e.g. a blood vessel such as an artery) that is connected to and provides access to the organ that is to be preserved. Introduction of the cold solution into the isolated segment of the biological conduit results in perfusion of the organ with the cold solution, and initiation of the preservation process. The method, which requires a minimum of supplies and equipment, can be implemented rapidly in a variety of settings. Use of the novel methods and flushing solutions results in maintenance of the viability of the internal organs until they can be further processed and readied for transplantation into a waiting recipient.

It is an object of this invention to provide a method of preserving an organ in-situ for bridging the time period from organ availability until organ harvest can occur. The method comprises the steps of i) identifying a suitable non-heart beating donor (NHBD); ii) introducing an artificial conduit into a biological conduit of said NHBD, the biological conduit containing at least one connection to the organ, the connection allowing passage of fluid from the biological conduit into the organ; and iv) flushing a chilled preservation solution into the biological conduit via said artificial conduit, wherein the step of flushing causes the chilled preservation solution to pass from the biological conduit through the connection and into the organ, thereby cooling and preserving the organ. The preservation solution comprises agents for mitigating cellular damage caused by warm and cold ischemia and reperfusion injury. The method may also include the step of isolating a region within the NHBD which is accessed by the biological conduit and which includes the organ and the at least one connection, and which excludes other organs of the NHBD. This step of isolation is preferred in some embodiments but is not always essential. The organs that may be preserved by the methods of the invention include but are not limited to kidney, liver, heart, and pancreas. In one embodiment, the agents in the solution include agents which include but are not limited to: agents that prevent cytoskeletal disassembly, agents that precondition, agents that protect mitochondrial function, agents that reduce membrane permeability, and agents that activate survival pathways. In one embodiment of the invention, the preservation solution comprises 0-15 mM butyrate,
5-20 mM $KH_2PO_4$,
10-50 mM $NaH_2PO_4$,
0-200 mM maltitol,
0-20 mM glucose,
0-200 mM sucrose,
0-5 mM pentoxifylline,
0-10 µM lysophosphatidic acid,
0-200 µM diazoxide
0-10 mM adenosine,
0-10 mM glycine,
0-5% polyethylene glycol-8000,
0-50 mM HEPES,
0-500 nM 16,16-Dimethyl $PGE_2$,
0-50 µM anisomycin,
0-2×RPMI Amino Acid Mix,
0-200,000 U/L penicillin,
0-20,000 U/L heparan sulfate; and
0-10 mM dichloroacetate.

In another embodiment, the preservation solution comprises:
10 mM butyrate,
5 mM $KH_2PO_4$,
25 mM $NaH_2PO_4$,
100 mM maltitol, 10 mM glucose,
100 mM sucrose,
3 mM pentoxifylline,
1 μM lysophosphatidic acid,
100 μM diazoxide
5 mM adenosine,
5 mM glycine,
1.5% polyethylene glycol-8000,
10 mM HEPES,
60 nM 16,16-Dimethyl $PGE_2$,
10 μM anisomycin,
1×RPMI Amino Acid Mix,
200,000 U/L penicillin,
20,000 U/L heparan sulfate; and
5 mM dichloroacetate.

The invention further provides a solution for organ preservation that comprises: agents that prevent cytoskeletal disassembly; agents that precondition; agents that protect mitochondrial function; agents that reduce membrane permeability; agents that activate survival pathways; and a physiological carrier. In some embodiments, the solution may also include agents that cause vasodialation and anti-inflammatory agents. In one embodiment, the solution comprises:

0-15 mM butyrate,
5-20 mM $KH_2PO_4$,
10-50 mM $NaH_2PO_4$,
0-200 mM maltitol,
0-20 mM glucose,
0-200 mM sucrose,
0-5 mM pentoxifylline,
0-10 μM lysophosphatidic acid,
0-200 μM diazoxide
0-10 mM adenosine,
0-10 mM glycine,
0-5% polyethylene glycol-8000,
0-50 mM HEPES,
0-500 nM 16,16-Dimethyl $PGE_2$,
0-50 μM anisomycin,
0-2×RPMI Amino Acid Mix,
0-200,000 U/L penicillin,
0-20,000 U/L heparan sulfate; and
0-10 mM dichloroacetate.

In another embodiment, the solution comprises:
10 mM butyrate,
5 mM $KH_2PO_4$,
25 mM $NaH_2PO_4$,
100 mM maltitol,
10 mM glucose,
100 mM sucrose,
3 mM pentoxifylline,
1 μM lysophosphatidic acid,
100 μM diazoxide
5 mM adenosine,
5 mM glycine,
1.5% polyethylene glycol-8000,
10 mM HEPES,
60 nM 16,16-Dimethyl $PGE_2$,
10 μM anisomycin,
1×RPMI Amino Acid Mix,
200,000 U/L penicillin,
20,000 U/L heparan sulfate; and
5 mM dichloroacetate.

DETAILED DESCRIPTION OF THE PREFERRED EMBODIMENTS OF THE INVENTION

Figure 1:
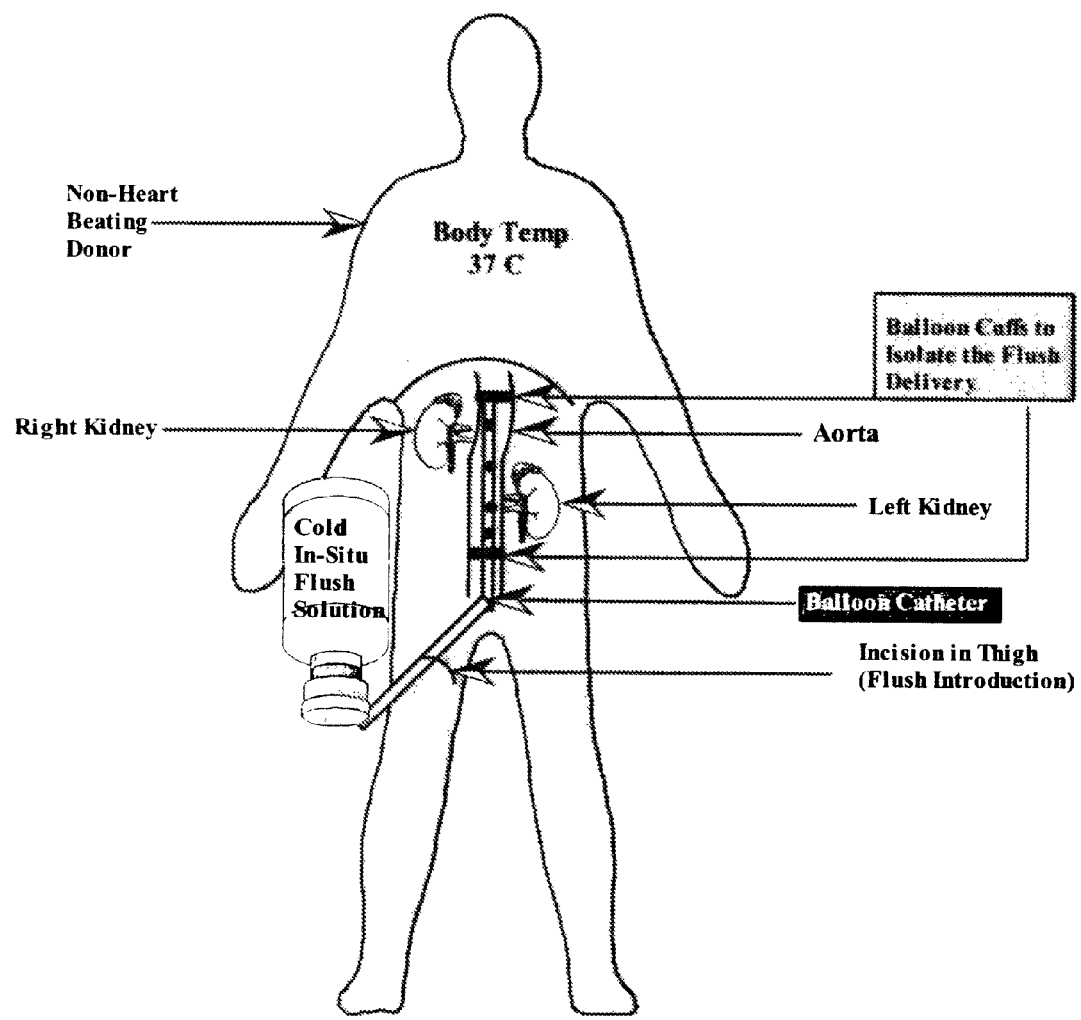
FIG. 1. Diagrammatic representation of the delivery of an in-situ organ flush after cardiac death. The in-situ flush is delivered by a catheter inserted in an artery in the groin to begin the cool down and to deliver the flush to the kidneys immediately after cardiac death.

The present invention is based on the discovery that the viability of internal organs with respect to their use for organ transplant can be preserved by the rapid, in-situ introduction of cooling solutions into the organs in NHBD organ donors. In other words, the preservation process begins prior to removal of the organ from the donors body, thereby buying valuable time until conventional organ harvest and preservation procedures can be implemented. In some embodiments, delivery of the solution is carried out using established medical techniques (e.g. catheter placement) and thus does not require additional specialized equipment or training of personnel. Thus, the methods are accessible to medical personnel in a variety of settings. The benefits or using the methods are profound: internal organs that would otherwise be vitiated by the effects of warm ischemia are instead preserved and may be used for transplant into a waiting recipient. In addition, the solutions that are used to flush the organs are also novel. Known flushing solutions (e.g. Viaspan®, MPS® and Celsior®) work predominantly by preventing cell swelling using cell impermeants. In contrast, the flushing solutions of the present invention include components that target basic mechanisms of cell injury during ischemia and activate known biochemical survival pathways in the cell. This novel procedure of bridging warm ischemic organs with minimally invasive techniques via in-situ preservation provides the time required for conventional organ harvest and/or preservation to begin.

As a first step to carrying out the method, a suitable non-heart beating donor must be identified. Those of skill in the art are familiar with the criteria for identifying such donors, which involves determining that irreversible cardiac death has occurred in an individual. Such a determination is typically made by trained medical personnel after repeated, exhaustive attempts to revive an individual (e.g. cardiopulmonary resuscitation, defibrillation, fluid resuscitation, drugs, etc) have failed. The method of the invention should be carried out as soon as possible after such a determination has been made. Generally, the method should be carried out within a time frame of from about 30 minutes to about 90 minutes after cardiac death, and preferably within a time frame of from about 10 minutes to about 30 minutes after cardiac death.

Once a suitable donor is identified, preservation of an organ of interest within the donor is initiated by administering a cold flushing solution to the organ, generally while the organ is still within the body of the donor, i.e. "In-situ". In order to do so, in some embodiments of the invention, the method takes advantage of the body's natural architecture, especially natural, biological distribution systems (biological conduits) that are adapted to the containment, routing and delivery of liquids within the body. The solution is thus administered to the organ indirectly by first introducing it into such a system. The biological conduit into which the solution is introduced must be "connected to" the organ that is to be preserved, for example, via an opening or luminal connection such as a blood vessel, or other canal or duct, etc., that allows the solution to pass from the biological conduit to the organ. The circulatory system is one such exemplary system, and in one embodiment of the invention, the biological conduit into which the flushing solution of the invention is introduced is an artery. For example, in the case a preferred embodiment of in-situ preservation of kidneys, the cold flushing solution, may be introduced into the abdominal aorta, and from thence directed to the kidneys by flowing through the natural system of blood vessels between the aorta and the kidneys.

However, those of skill in the art will recognize that the practice of the invention is in no way limited to introduction of the flushing solution by means of an artery. Depending on the organ(s) to be preserved, and other considerations (such as the equipment that is available, the availability and condition of portions of the donors body, etc.) other natural conduits may also be utilized. Such natural conduits include but are not limited to flushing the liver through the portal vein by access through a TIPPS procedure or other access points (e.g. intestinal vein); flushing the intestines via the lumen using, for example, a jejunostomy catheter; or flushing the heart with a femoral catheter; etc. Further, in some embodiments of the invention, delivery of the solution to an organ or organs from conventional brain dead organ donors may be by intra-operative perfusion of the solution directly into the abdominal aorta and then around the organ while in storage (conventional multi-organ harvest) or delivered directly into the single aorta/vein perfusing the organ after surgical recovery from living or living related donors (e.g. living kidney/liver harvest).

Introduction of the cold flushing solution may be accomplished by any suitable means, many of which will occur to those of skill in the art. In some embodiments, introduction of the solution is accomplished using an artificial conduit such as a catheter with either gravity feed or pump assist. Those of skill in the medical arts are familiar with such artificial conduits, and with the procedures for inserting them into the body, and for administering solutions through, such conduits. Taking kidney preservation as an example, a double balloon Garcia-Lafrack or similar type catheter may be inserted into the abdominal aorta via an incision in the thigh or groin, and the flushing solution delivered to the aorta there through. In the case of the pancreas and/or small bowel, access via the femoral artery may be accomplished by altering the position of the balloon catheter in the aorta to accommodate flush delivery through the celiac axis. The liver could be accessed by the portal vein via a trans-jugular intra-hepatic portal systemic shunt (TIPSS) procedure or via an intestinal vein. For preservation of the heart, administration may be into the coronary arteries via the ascending aorta with a single balloon catheter occluded proximal to the effluent flow. This catheter position is accessed by insertion through the right common carotid artery or the femoral artery, as examples.

In the practice of the invention, it is preferable to limit dissemination of the flushing solution into areas other than the organ(s) of interest in order to maximize cooling and delivery of the flush active components. Such dissemination may be prevented or minimized, for example, by isolating a suitable segment of the biological conduit into which the solution is delivered. For example, when the biological conduit is an artery, the solution can be confined to a suitable region of the artery by blocking off one or more isolated segments or regions of the artery. This may be accomplished by blocking the artery by any of several known methods. For example, when the artificial conduit is a catheter, and the organ to be perfused is the kidney, inflatable balloon cuffs that span the outflow holes of the catheter are provided. Inflation of the balloon cuffs occludes the aorta at locations on either side of the blood vessels that connect to the kidneys. When the cold flushing solution is introduced into the isolated section of the aorta, the predominant remaining route of flow for the liquid is through the blood vessels leading to the kidneys, and into the kidneys. By appropriately isolating selected regions of a biological conduit, the flushing solution can thus be delivered selectively to one or more organs of interest. The solution is exited, thereby promoting delivery, by venting the outflow through an appropriate venous drainage route (e.g. a catheter inserted into the femoral vein in the case of in-situ kidney harvest. The outflow is then allowed to drain into a container outside of the patient, thus improving the gradient for inward flow of the flush solution.

In order to effect rapid cooling of the organ in-situ, the flushing solution (or components thereof) are generally stored in the cold and/or chilled prior to use. In general, the temperature of the solution when used should be in the range of about 10° C. to about 2° C., and preferably as cold as possible, e.g. from about 2° C. to about 0° C. Those of skill in the art will recognize that, depending on circumstances (such as the size of the organ, the availability of equipment and personnel to carry out the next steps of organ preservation and/or transplant, etc.), the amount of solution that is used to flush an organ may vary. In general, the amount of flushing solution that is introduced into the organ is about 100-200 ml per kg of total body weight such that the temperature of the organs of interest reach a temperature of about 25° C.

Similarly, the length of time of the flush may vary depending on the organ of interest. In general, so long as a suitable minimum volume of solution is delivered to achieve a temperature drop of about 12 degrees C., as described above, the organ (e.g. kidney) will remain viable for at least about 1 hour, and for as long as about 3 hours before conventional organ harvest is initiated. Preferably, the organ will be moved into the next stage of preservation/transplantation at from about 1 to about 2 hours after bridge flushing is completed. Typically, the temperature of the organ after flushing is about 26 to about 20° C., depending of the amount of flush delivered and the efficiency of the flush proceeding.

Typically, after the flushing solution is introduced into the organ, the liquid that is displaced from the organ by the flushing solution and the excess flushing solution that passes through the organ exits the organ via passages or ducts that are naturally present therein. Such fluids may be further directed to exit the donor body by any convenient means, e.g. via a natural opening, or an opening that is surgically provided, or a second catheter, etc., and will typically be directed to a waste container.

After the bridge flushing procedure is completed, the organs may be subjected to known conventional preservation methods, e.g. direct removal from the body, hypothermic pulsatile machine perfusion, etc. Those of skill in the art are well-acquainted with such procedures. The invention provides the time necessary to get an organ harvest and/or transplant team assembled to harvest an organ i.e. tracking a dying patient is not required. The invention bridges this time period by preserving and protecting the cells in the organ form damage.

The flushing solutions of the invention are also novel, and are formulated to overcome several problems associated with damage from ischemia and damage from cooling. For example, the low temperature of the flush lowers the tissue temperature of the perfused organ, which lowers metabolic demand and preserves tissue energy stores and function. In general the temperature of the flushing solution when used will be in the range of from about 6° C. to about 2° C., and preferably from about 2° C. to about 0° C. However, cooling of tissue in and of itself can also damage tissue by causing tissue swelling. In the solutions of the present invention, this is addressed by inclusion in the solution of impermeant saccharides, examples of which include sucrose, maltitose, and polyethylene glycol (PEG)-8000. In addition, the flushing solution of the invention includes components that are known to activate preconditioning and activate survival pathways in cells. Activation of these pathways promotes resistance to the effects of energy depletion, and osmotic and oxidative stress that the cells encounter after cardiac death (e.g. warm ischemia, reperfusion injury, hypothermia, etc.). Strengthening of the cell cytoskeletal system and other crucial cellular components help to achieve this. The precise mechanism of action of such agents is not necessarily distinct, since the activity of the agents may overlap. However, a description of the composition of an exemplary flushing solution (in particular for use in kidney preservation), and the rationale for the inclusion of the listed agents, is given in Table 1. In Table 1, Column I lists exemplary components of a preferred solution, Column II gives the suggested concentration of each component in one exemplary flushing solution, Column II gives suggested approximate variations in the ranges of the suggested components, and Column IV lists the known function of each component, it being understood that other chemical that perform these functions can be used in the practice of the invention. As can be seen, the solution is formulated to protect the cell from swelling that occurs during both hypothermia and ischemia. In addition, and in contrast to known preservation solutions, the flushing solution of the present invention also includes agents to activate pro-survival biochemical pathways that induce tolerance to further stress encountered during the warm and cold ischemia and preservation periods. Examples of such agents include but are not limited to: agents that increase cAMP levels, agents that prevent cytoskeletal disassembly, agents that precondition, agents that protect mitochondrial activity, agents that are a source of ATP production, vasodialators, agents that activate survival pathways, agents that reduce membrane permeability, and anti-inflammatory agents. Of particular note are agents that prevent cytoskeletal disassembly, agents that precondition, agents that protect mitochondrial function, agents that reduce membrane permeability, and agents that activate survival pathways. Thus, while the organ is without blood flow and oxygenation, ATP degradation is slowed and resistance to cell stress and death is greatly activated. This enhances organ function at transplantation (reperfusion) since the organ suffers less injury from the cardiac death and donation processes (warm ischemia).

TABLE 1

Composition of In-Situ Preservation (ISP) Bridge Solution

| I. Component | II. Concentration | III. Range | IV. Function |
|---|---|---|---|
| Butyrate | 10 mM | 0-15 mM | Energy source |
| $KH_2PO_4$ | 5 mM | 5-20 mM | Buffer; $PO_4$ source (ATP) |
| $NaH_2PO_4$ | 25 mM | 10-50 mM | Buffer; $PO_4$ source (ATP) |
| Maltitol | 100 mM | 0-200 mM | Cell impermeant, prevent cell swelling |
| Glucose | 10 mM | 0-20 mM | Energy source |
| Sucrose | 100 mM | 0-200 mM | Cell impermeant, prevent cell swelling |
| Pentoxifylline | 3 mM | 0-5 mM | Increase cAMP, precondition |
| Lysophosphatidic acid | 1 μM | 0-10 μM | Prevent cytoskeletal dissambly |
| Diazoxide | 100 μM | 0-200 μM | Protect mitochondria, precondition |
| Adenosine | 5 mM | 0-10 mM | Precondition, ATP source, stabilize cytoskeleton |
| Glycine | 5 mM | 0-10 mM | Protect cell membrane |
| Polyethylene Glycol-8000 | 1.5% | 0-5% | Protect cell membranes, prevent cell swelling |
| HEPES | 10 mM | 0-50 mM | Buffer |
| 16,16-Dimethyl $PGE_2$ | 60 nM | 0-500 nM | Vasodialotor, cytoprotectant, |
| Anisomycin | 10 μM | 0-50 μM | Activate p38 survival pathways |
| *RPMI Amino Acid Mix (5x) | 1x | 0-2x | Protein synthesis, cytoprotectant |
| Penicillin | | 0-200,000 U/L | Control/prevent infection |
| Heparan Sulfate | | 0-20,000 U/L | Anticoagulant, anti-inflammatory |
| Dichloroacetate | 5 mM | 0-10 mM | Energy production |

*RPMI amino acid mix, available from Sigma Chemical Co. Composition is given in Table 2.

TABLE 2

Composition of RPMI amino acid mix from Sigma Chemical Co. 20 ml/L of a 50x stock solution is used.

| Amino Acid | Concentration (g/L) |
|---|---|
| L-Arginine | 10 |
| L-Asparagine | 2.84 |
| L-Aspartic acid | 1.0 |
| L-Cysteine | 2.5 |
| L-Glutamic acid | 1.0 |
| Glycine | 0.5 |
| L-Histidine | 0.75 |
| Hydroxy-L-Proline | 1.0 |
| L-Isoleucine | 2.5 |
| L-leucine | 2.5 |
| L-Lysine-HCl | 2.0 |
| L-Methionine | 0.75 |
| L-Phenylalanine | 0.75 |
| L-Proline | 1.0 |
| L-Serine | 1.5 |
| L-Threonine | 1.0 |
| L-Tryptophan | 0.25 |
| L-Tyrosine | 1.16 |
| L-Valine | 1.0 |

The flushing solution generally comprises a physiological carrier, e.g. a liquid that serves to maintain the solution at physiologically relevant pH and tonicity, and thus to prevent, for example, the bursting of red blood cells. Such carriers are well known.

In general, the flushing solution is adjusted to and maintained at a physiologically compatible pH, e.g. in the range of about 6.8 to about 7.6, and preferably at about pH 7.2. The solution is sterilized, e.g. by exclusion filtration or other suitable means, and should be stored at 0-6° C. until use. The $PGE_2$ analog (16,16-Dimethyl $PGE_2$) is preferably sterilized and stored separately at −80° C., and added to the final solution immediately before use. Alternatively, this agent may also be lyophilized in a small vial or other compartment and attached to the container that holds the solution, to be stored therewith and reconstituted directly before use (e.g. in a bubble compartment on a Viaflex bag containing the flush solution.) These procedures will maintain the integrity of the PGE analog during storage and ensure its full biological activity at the time of use.

Those of skill in the art will recognize that the suggested composition in Table 1 is illustrative, and that the ingredients and the concentrations may vary and still be successfully used as a flushing solution. In general, the composition will include compounds with the functions indicated in Table 1, namely one or more of: energy sources or promoters of ATP synthesis, examples of which include but are not limited to: ademosine, phosphates, butyrate, glucose, amino acids, and dichloroacetate; buffers such as potassium or sodium-phosphate salts, HEPES, aminos acids, etc.; $PO_4$ sources for ATP synthesis such as potassium or sodium-phosphate salts; cell impermeants such as maltitol, glucose, sucrose, and PEG-8000; agents that increase cAMP such as pentoxifylline, and $PGE_2$ analogs; anti-inflammatory agents such as 16,16-dimethyl $PGE_2$, pentoxifylline, heparin sulfate, and adenosine; cytoskeletal stabilizing agents such as lysophosphatidic acid, diazoxide, adenosine, glycine, PEG-8000, and anisomycine; agents that protect mitochondria such as malititol, sucrose, diazoxide, glycine, PEG-8000; preconditioning agents such as pentoxyfylline, lysophosphaticid acid, diazoxide, adenosine, and anisomycine; agents that protect the cell membrane such as glycine, PGE, PEG-8000; vasodialators such as pentoxyfylline, 16,16-dimethyl $PGE_2$; agents that activate survival pathways such as aniomycine, lysophosphatidic acid; various amino acids; agents that inhibit bacterial or fungal growth such as antibiotics (e.g. penicillin, anisomycine); anticoagulants such as heparin sulfate; agents that modulate energy production such as dichloroacetate; etc.

Variations in the precise identity and concentration of components in the solution may vary somewhat, depending on, for example, the particular organ to be preserved. For example, in the case of liver and pancreas preservation (especially if initial preservation endures for more than about 4 hours), it may be desirable to utilize cell permeants with larger molecular weight (e.g. raffinose and/or trehalose), as these organs are more permeable to smaller saccharides such as sucrose and glucose. Nevertheless, since exposure to the flushing solution can be relatively short (e.g. about 1-4 hours, or until conventional preservation/transplant procedures are set in motion), the effects of smaller saccharides may be inconsequential. Those of skill in the art are familiar with techniques that can be used to optimize solution composition for different organ types. For example, see Southard and Belzer, Principles of Organ Preservation I, *Surgical Rounds*, May: 353-360, 1993; and Southard and Belzer, Principles of Organ Preservation II, *Surgical Rounds*, June: 443-449, 1993.

One advantage of method of the invention is that it requires a minimal amount of supplies and equipment, and can readily be carried out in a variety of clinical settings. Such settings include but are not limited to emergency rooms, trauma wards, operating theaters, delivery rooms, etc., where there is a possibility or likelihood of being able to identify suitable non-heart beating donors. However, those of skill in the art will recognize that the method may also be carried out by trained specialists (e.g. emergency medical technicians, first responders) in the field (i.e. "out of hospital") in settings such as in an ambulance, at accidents sites, etc. The method requires chiefly the availability of the cold flushing solution and equipment for introducing the solution into body of the donor as described herein.

Those of skill in the art will recognize that many organs can be processed by the methods described herein in order to preserve them for transplantation. Examples include but are not limited to abdominal organs such as kidney, liver, pancreas, intestines; the heart and lungs in the thoracic cavity, etc. The solution and its delivery are well suited for non-transplant related flush procedures where the metabolic demands of the tissue need to be reduced and the effects of hypothermia diminished. A primer example includes the regional intravascular cooling of the brain during complex cardiac and cardiovascular procedures where cooling of the brain is required while blood flow is stopped to repair the heart or its major blood vessels. In short, any organ that is or can be made accessible to the flushing solution can be treated by the methods of the invention. In addition, the methods need not be applied to an organ per se. Rather, other types of structure, e.g. tissues such as nerve, connective tissue, pancreatic tissue for islet processing and isolation, resected liver tissue for hepatocyte isolation; body parts or mixed tissue transplants such as digits (fingers, toes), limbs, hands, facial tissue, etc. may also be treated according to the methods of the invention in order to promote viability. The delivery of the flush under these conditions may also be by conventional flushing procedure and not necessarily by minimally invasive in-situ techniques. In addition, more than one organ or body part may be preserved in a NHBD at a time using the methods described herein. For example, the isolated region of the aorta may include access to both the kidneys and the hepatic artery of the liver in the same flushing procedure, or multiple isolated regions may be flushed separately but concomitantly, an example being the aorta for the renal artery (kidney) and the hepatic arteries of the liver via one cannula in the aorta and the portal system (liver) via a separate cannula at the same time.

Further, with respect to the solutions of the invention, while preferred uses involve NHBDs, this need not be the case. Organs taken from living donors may also benefit from being flushed by the unique solutions provided herein, albeit such flushing would generally not be carried out in-situ. The methods of the invention may be especially appropriate for preservation and support of organs from extended criteria donors, e.g. older donors, or unstable donors, or from donors with cardiovascular or metabolic disease. Organs from such donors typically do not do well and may benefit greatly from the support provided by the flushing solutions of the invention. In addition, the fate of the organs so preserved need not necessarily be transplantation. Much benefit may accrue, for example, from the availability of well-preserved organs for purposes such as research or teaching, or for storage for prolonged periods of time.

In general, the organs that are treated according to the invention are mammalian in origin, and may be human. However this need not be the case. The invention may also be used in veterinary applications or in interspecies transplant events. In these applications, the choice of constituents in the flushing solution may vary depending on the animal. However, the function fulfilled by the constituents that are employed will be similar to that set forth above in Table 1.

The practice of the invention is further illustrated by the following non-limiting examples.

EXAMPLES

Example 1

In-Situ Kidney Flush in a Non-Heart Beating Donor (NHBD)

A suitable NHBD is identified as being in irreversible cardiac death after prolonged but failed attempts at resuscitation by CPR in the emergency room. As soon thereafter as possible, and as schematically illustrated in FIG. 1, a balloon catheter is introduced in the femoral artery in the groin and advanced into the abdominal aorta. Two balloon cuffs span the outflow holes in the catheter and once the catheter is properly positioned, the balloons are inflated so that the balloons isolate the outflow holes of the catheter at the level of both renal arteries.

Cold in-situ flush solution is introduced through the catheter and into the abdominal artery. Once the flush is started, the solution floods the isolated section of aorta, which perfuses the two renal arteries feeding the right and left kidneys. An insignificant amount of flush will be directed into the spinal cord through the vertebral artery branches, but sufficient liquid is provided to also completely perfuse the kidneys. Approximately 4-12 liters of cold in-situ flush solution is required to effectively cool and equilibrate both kidneys in a 70 kg adult donor. The flush drains through the kidneys into the right and left renal veins and into the infra-hepatic inferior vena cava and it allowed to exit the patient via a femoral vein catheter open to atmosphere and directed into a waste reservoir. This procedure accomplishes two objectives: first, the kidneys begin to cool down within 10-30 minutes after cardiac death to slow metabolism and preserve kidney function; second, the biochemical components of the flush, which are designed to protect the organ during the ischemia phase, are delivered to the kidneys where equilibration with the cellular components of the kidneys occurs.

Figure 2:
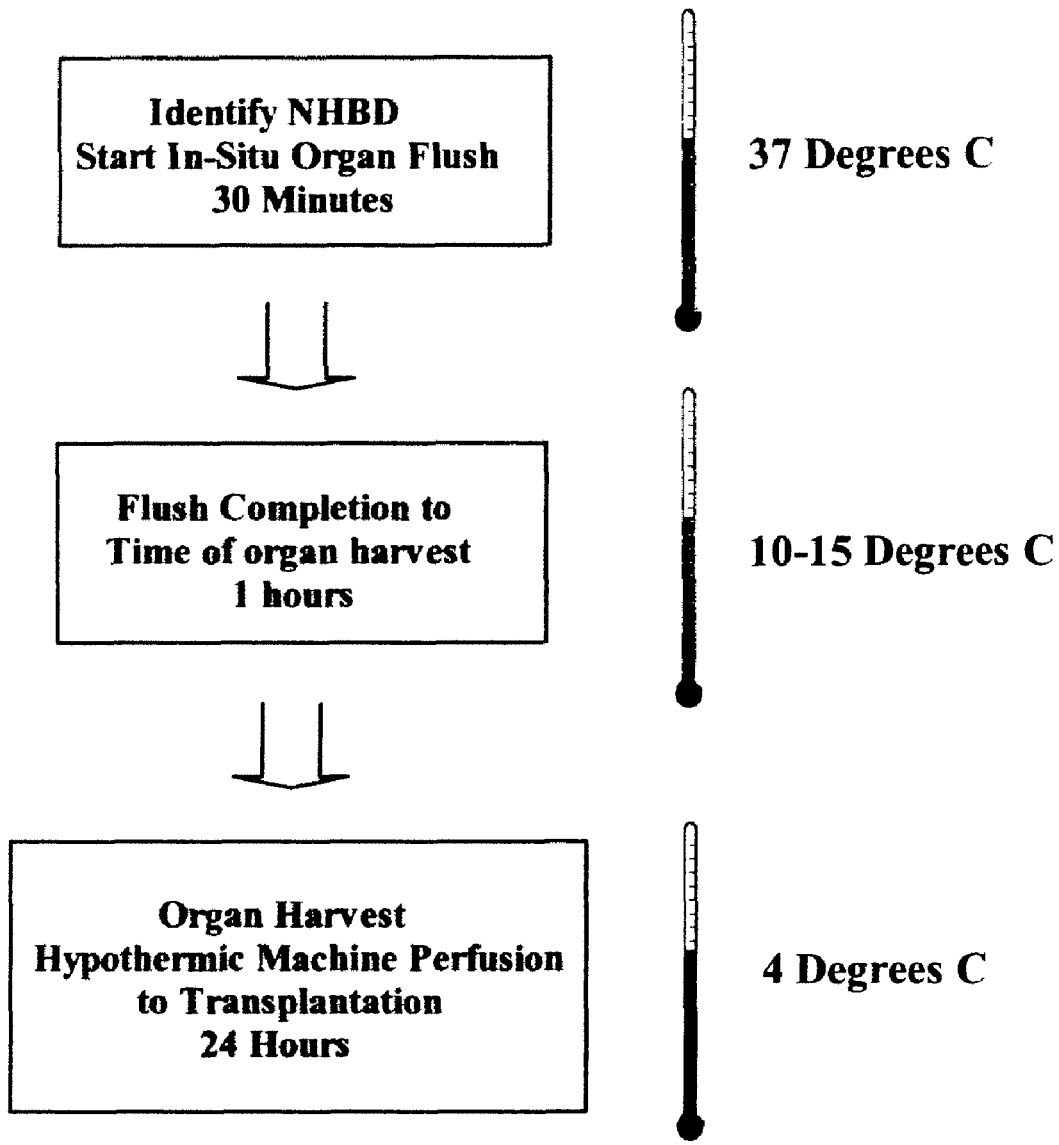
FIG. 2. Time and temperature flow chart of kidneys during in-situ preservation.

A general time course of the procedure is shown in FIG. 2, and demonstrates the rapid reduction in temperature that is achieved during flush delivery. If conventional donor harvesting procedures were used in a non-heart beating donor, this level of cooling would typically not occur until well after 90-180 minutes of warm ischemia, by which time the kidneys would be unsuitable for transplant. In contrast, by utilizing the method of the present invention, the period of time between the earliest availability of an organ and the time when the organ is finally removed from a body for transplant is "bridged", and this bridge time can be from about 0.5 to 5 hours, and preferably up to about 3 hours, while personnel and equipment for further transplant/preservation procedures are put into place.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

I claim:

1. A solution for organ preservation, comprising each of:
   butyrate,
   $KH_2PO_4$,
   $NaH_2PO_4$,
   maltitol,
   glucose,
   sucrose,
   pentoxifylline,
   lysophosphatidic acid,
   diazoxide
   adenosine,
   glycine,
   polyethylene glycol-8000,
   HEPES,
   16,16-Dimethyl $PGE_2$,
   anisomycin,
   RPMI Amino Acid Mix,
   penicillin,
   heparan sulfate; and
   dichloroacetate.

2. The solution of claim 1, comprising
   10 mM butyrate,
   5 mM $KH_2PO_4$,
   25 mM $NaH_2PO_4$,
   100 mM maltitol,
   10 mM glucose,
   100 mM sucrose,
   3 mM pentoxifylline,
   1 µM lysophosphatidic acid,
   100 µM diazoxide
   5 mM adenosine,
   5 mM glycine,
   1.5% polyethylene glycol-8000,
   10 mM HEPES,
   60 nM 16,16-Dimethyl $PGE_2$,
   10 µM anisomycin,
   20 ml/L of a 50×RPMI Amino Acid Mix,
   200,000 U/L penicillin,
   20,000 U/L heparan sulfate; and
   5 mM dichloroacetate.

3. A method of preserving an organ in-situ for bridging the time period from organ availability until organ harvest can occur, comprising the steps of
   identifying a suitable non-heart beating donor (NHBD);
   introducing an artificial conduit into a biological conduit of said NHBD, said biological conduit containing at least one connection to said organ, said connection allowing passage of fluid from said biological conduit into said organ; and
   flushing a chilled preservation solution into said biological conduit via said artificial conduit, wherein said step of flushing causes said chilled preservation solution to pass from said biological conduit through said connection and into said organ, thereby cooling and preserving said organ,
   wherein said preservation solution comprises agents for mitigating cellular damage caused by warm and cold ischemia and reperfusion injury,
   wherein said preservation solution comprises each of
   butyrate,
   $KH_2PO_4$,
   $NaH_2PO_4$,
   maltitol,
   glucose,
   sucrose,
   pentoxifylline,
   lysophosphatidic acid,
   diazoxide
   adenosine, glycine,
polyethylene glycol-8000,
HEPES,
16,16-Dimethyl $PGE_2$,
anisomycin,
RPMI Amino Acid Mix,
penicillin,
heparan sulfate; and
dichloroacetate.

4. The method of claim 1, wherein said preservation solution comprises
10 mM butyrate,
5 mM $KH_2PO_4$,
25 mM $NaH_2PO_4$,
100 mM maltitol,
10 mM glucose,
100 mM sucrose,
3 mM pentoxifylline,
1 µM lysophosphatidic acid,
100 µM diazoxide
5 mM adenosine,
5 mM glycine,
1.5% polyethylene glycol-8000,
10 mM HEPES,
60 nM 16,16-Dimethyl $PGE_2$,
10 µM anisomycin,
20 ml/L of a 50×RPMI Amino Acid Mix,
200,000 U/L penicillin,
20,000 U/L heparan sulfate; and
5 mM dichloroacetate.

* * * * *